(12) United States Patent
Vogel

(10) Patent No.: US 6,872,844 B2
(45) Date of Patent: Mar. 29, 2005

(54) METAL COMPLEXES CONTAINING ACETYLENIC LIGANDS, POLYMERIZATION CATALYSTS AND ADDITION POLYMERIZATION PROCESS

(75) Inventor: Alexander Vogel, Houston, TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 10/468,531

(22) PCT Filed: Feb. 8, 2002

(86) PCT No.: PCT/US02/03702

§ 371 (c)(1),
(2), (4) Date: Aug. 19, 2003

(87) PCT Pub. No.: WO02/074779

PCT Pub. Date: Sep. 26, 2002

(65) Prior Publication Data

US 2004/0082769 A1 Apr. 29, 2004

Related U.S. Application Data

(60) Provisional application No. 60/277,105, filed on Mar. 19, 2001.

(51) Int. Cl.$^7$ ............... C07F 17/00; B01J 31/00; C08F 4/44

(52) U.S. Cl. ............... 556/11; 556/12; 556/20; 556/21; 556/43; 556/47; 556/53; 556/58; 502/103; 502/117; 502/120; 526/160; 526/943

(58) Field of Search ............... 556/11, 12, 20, 556/21, 43, 47, 53, 58; 502/103, 117, 120; 526/160, 943

(56) References Cited

PUBLICATIONS

Foerstner et al., Journal of Organometallic Chemistry, vol. 617–618, pp. 412–422 (Jan. 15, 2001).*
Foerstner et al., Organometallics, vol. 19, pp. 2108–2113 (Apr. 28, 2000).*

* cited by examiner

*Primary Examiner*—Porfirio Nazario-Gonzalez

(57) ABSTRACT

A complex of a Group 3-10 metal, said complex comprising a cyclic group containing delocalized electrons, a bridging group connecting he metal with the cyclic group, and acetylene or a derivative thereof.

11 Claims, No Drawings

METAL COMPLEXES CONTAINING ACETYLENIC LIGANDS, POLYMERIZATION CATALYSTS AND ADDITION POLYMERIZATION PROCESS

This application claims the benefit of Provisional Application No. 60/277,105, filed Mar. 19, 2001.

This invention relates to a class of metal complexes and to addition polymerization catalysts derived from such complexes that are particularly suitable for use in a polymerization process for preparing homopolymers and copolymers of olefins or diolefins, including copolymers comprising two or more olefins or diolefins such as copolymers comprising a monovinyl aromatic monomer and ethylene or a $C_{3-8}$ α-olefin and ethylene.

Constrained geometry metal complexes and methods for their preparation are disclosed in U.S. Pat. No. 5,703,187. Additional teachings of constrained geometry catalysts may be found in U.S. Pat. Nos. 5,321,106, 5,721,185, 5,374,696, 5,470,993, 5,541,349, and U.S. Pat. No. 5,486,632. Such metal complexes containing a neutral conjugated diene ligand group are disclosed in U.S. Pat. Nos. 5,470,993, 5,556,928 and 5,624,878.

Certain highly active, polyaromatic, metal complexes, especially derivatives of cyclopentaphenanthrenyl ligand groups are disclosed in U.S. Pat. No. 6,150,297. Metallocenes containing multiple, non-aromatic fused ring systems are disclosed in U.S. application Ser. No. 09/879,463, filed Jun. 12, 2001.

According to the present invention there is provided a metal complex corresponding to the formula:

where Cp is a neutral or anionic ligand group containing at least on cyclic group containing delocalized π-electrons, by means of which Cp is bonded to M;

M is a metal selected from Groups 3-10 or the Lanthanide series of the Periodic Table of the Elements;

ZY is a linking group with Z bonded to Cp and Y bonded to M, and wherein Z is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, $SnR^6$, or $GeR^6_2$, and Y is —O—, —S—, —NR$^5$—, —PR$^5$—; —NR$^5_2$, or —PR$^5_2$;

$R^5$, independently each occurrence, is hydrocarbyl, trihydrocarbylsilyl, or trihydrocarbylsilylhydrocarbyl, said $R^5$ having up to 20 atoms not counting hydrogen, and optionally two $R^5$ groups together with the remainder of Y form a ring system;

$R^6$, independently each occurrence, is hydrogen, or a member selected from hydrocarbyl, hydrocarbyloxy, silyl, halogenated alkyl, halogenated aryl, —NR$^7_2$, and combinations thereof, said $R^6$ having up to 20 atoms not counting hydrogen, and optionally, one or more $R^6$ groups together with the remainder of Z form a ring system;

$R^7$ independently each occurrence is hydrocarbyl or two $R^7$ groups together with N form a ring system, said $R^7$ having up to 10 atoms not counting hydrogen;

L'' is a monodentate or polydentate Lewis base optionally bonded to $R^6$; and

L is acetylene, or a mono- or di-substituted derivative of acetylene.

The above compounds may exist as isolated crystals, as a mixture with other compounds, in the form of a solvated adduct, dissolved in a solvent, especially an organic liquid solvent, in the form of a dimer, or as a chelated derivative, especially wherein the chelating agent is an organic material such as ethylenediaminetetraacetic acid (EDTA).

Also, according to the present invention, there is provided a catalyst for addition polymerizations comprising:
A. i) a metal complex of formula (I), and
   ii) an activating cocatalyst,
the molar ratio of i) to ii) being from 1:10,000 to 100:1, or
B. the reaction product formed by converting a metal complex of formula (I) to an active catalyst by use of the foregoing combination or by use of an activating technique.

Further according to the present invention there is provided a process for the polymerization of addition polymerizable monomers, especially one or more olefins comprising contacting the monomer or mixture of monomers, under polymerization conditions with a catalyst comprising:
A. i) a metal complex of formula (I), and
   ii) an activating cocatalyst,
the molar ratio of i) to ii) being from 1:10,000 to 100:1, or
B. the reaction product formed by converting a metal complex of formula (I) to an active catalyst by use of the foregoing combination or by use of an activating technique.

Use of the present catalysts and processes is especially efficient in production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. They are especially useful for the formation of ethylene homopolymers, copolymers of ethylene and one or more higher α-olefins (that is, olefins having 3 or more carbon atoms), copolymers of ethylene, propylene and a diene (EPDM copolymers), copolymers of ethylene and vinylaromatic monomers such as styrene (ES polymers), copolymers of ethylene, styrene, and a diene (ESDM polymers), and copolymers of ethylene, propylene and styrene (EPS polymers). Examples of suitable diene monomers include ethylidenenorbornene, 1,4-hexadiene or similar conjugated or nonconjugated dienes. Surprisingly, the metal complexes of formula (II) demonstrate equivalent or improved catalytic properties compared to metal complexes containing polycyclic, fully aromatic, hydrocarbon ligands, and they and their degradation products are more biologically inert compared to compounds containing fused, polycyclic, fully aromatic hydrocarbon ligands.

The catalysts of this invention may also be supported on a solid material and used in olefin polymerization processes, including solution, slurry or gas phase polymerization processes. The catalyst may be used in combination with one or more additional polymerization catalysts including other metal complexes or conventional Ziegler-Natta catalysts, in the same or different polymerization reactors, operating in series or in parallel. Finally, the catalyst may be prepolymerized with one or more olefin monomers in situ in a polymerization reactor or in a separate process with intermediate recovery of the prepolymerized catalyst prior to the primary polymerization process.

In addition to their use as addition polymerization catalysts, complexes according to the present invention may be used for hydroformulation, hydrogenation or oligomerization processes.

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups. The contents of any patent, patent application or publication referenced herein is hereby incorporated by reference in its entirety herein, especially with respect to its disclosure of organometallic structures, synthetic techniques and general knowledge in the art. As used herein the term "aromatic" refers to a polyatomic, cyclic, ring system containing (4δ+2) π-electrons, wherein δ is an integer greater than or equal to 1. The term "fused" as used herein with respect to two polyatomic, cyclic rings means that such rings have two adjacent atoms thereof common to both rings. The term "fused" as used herein with respect to a ring system containing more than two polyatomic, cyclic rings, means that at least two rings thereof are fused together.

Desirably, in the compounds of the invention, Cp is a cyclopentadienyl group or a hydrocarbyl substituted derivative thereof, including fused multiple ring groups. Preferred L" groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms.

Preferred metal complexes of formula (I) correspond to the formula:

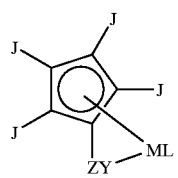

(IA)

wherein
M is a group 4 metal, preferably titanium;
Y is $NR^5$, wherein $R^5$ is $C_{1-10}$ alkyl or cycloalkyl;
Z is dimethylsilane;
J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and optionally two J groups together may form a divalent derivative thereby forming a saturated or unsaturated ring; and L is a disubstituted acetylene compound of the formula, J'C≡CJ', wherein J' is hydrocarbyl or tri(hydrocarbylsilyl) of up to 10 atoms not counting hydrogen, preferably trimethylsilyl. Because the ligand, L, is neutral, the Group 4 metal, preferably Ti, is in the +2 formal oxidation state.

The preparation of the metal complexes of formula (I) is straightforward, using standard techniques of ligand formation and organometallic synthesis. In one technique, the corresponding alkyl substituted metal complex is contacted with acetylene or a substituted acetylene in the presence of an oxidizing agent, especially an alkali metal compound.

Illustrative metal complexes that may be employed in the practice of the present invention include:

(tetramethylcyclopentadienyl)-N-(1,1-dimethylethyl) dimethylsilanamide titanium (II) 1,2-bis(trimethylsilyl) acetylene,
(tetramethylcyclopentadienyl)-N-(cyclohexyl) dimethylsilanamide titanium (II) 1,2-bis(trimethylsilyl) acetylene,
(inden-1-yl)-N-(1,1-dimethylethyl)dimethylsilanamide titanium (II) 1,2-bis(trimethylsilyl)acetylene,
(inden-1-yl)-N-(cyclohexyl)dimethylsilanamide titanium (II) 1,2-bis(trimethylsilyl)acetylene,
(2-methyl-4-phenylinden-1-yl)-N-(1,1-dimethylethyl) dimethylsilanamide titanium (II) 1,2-bis(trimethylsilyl) acetylene,
(2-methyl-4-phenylinden-1-yl)-N-(cyclohexyl) dimethylsilanamide titanium (II) 1,2-bis(trimethylsilyl) acetylene,
(2-methyl-4-naphthylinden-1-yl)-N-(1,1-dimethylethyl) dimethylsilanamide titanium (II) 1,2-bis(trimethylsilyl) acetylene,
(2-methyl-4-naphthylinden-1-yl)-N-(cyclohexyl) dimethylsilanamide titanium (II) 1,2-bis(trimethylsilyl) acetylene,
(3-(N,N-dimethylamino)inden-1-yl)-N-(1,1-dimethylethyl) dimethylsilanamide titanium (II) 1,2-bis(trimethylsilyl) acetylene,
(3-(N,N-dimethylamino)inden-1-yl)-N-(cyclohexyl) dimethylsilanamide titanium (II) 1,2-bis(trimethylsilyl) acetylene,
(3-(N,N-dimethylamino)inden-1-yl)-N-(1,1-dimethylethyl) dimethylsilanamide titanium (II) 1,2-bis(trimethylsilyl) acetylene,
(3-(N-pyrrolidino)inden-1-yl)-N-(cyclohexyl) dimethylsilanamide titanium (II) 1,2-bis(trimethylsilyl) acetylene,
(3-(N-pyrrolidino)inden-1-yl)-N-(1,1-dimethylethyl) dimethylsilanamide titanium (II) 1,2-bis(trimethylsilyl) acetylene,
(3-(N,N-dimethylamino)inden-1-yl)-N-(cyclohexyl) dimethylsilanamide titanium (II) 1,2-bis(trimethylsilyl) acetylene,
(s-inden-1-yl)-N-(1,1-dimethylethyl)dimethylsilanamide titanium (II) 1,2-bis(trimethylsilyl)acetylene,
(s-inden-1-yl)-N-(cyclohexyl)dimethylsilanamide titanium (II) 1,2-bis(trimethylsilyl)acetylene,
(3,4-(cyclopenta(l)phenantrathen-2-yl)-N-(1,1-dimethylethyl)dimethylsilanamide titanium (II) 1,2-bis(trimethylsilyl)acetylene,
(3,4-(cyclopenta(l)phenantrathen-2-yl)-N-(cyclohexyl) dimethylsilanamide titanium (II) 1,2-bis(trimethylsilyl) acetylene,
(2,8-dihydrodibenzo[e,h]azulen-2-yl)-N-(1,1-dimethylethyl)dimethylsilanamide titanium (II) 1,2-bis(trimethylsilyl)acetylene, and
(2,8-dihydrodibenzo[e,h]azulen-2-yl)-N-(cyclohexyl) dimethylsilanamide titanium (II) 1,2-bis(trimethylsilyl) acetylene,
and mixtures thereof, especially mixtures of positional isomers.

The skilled artisan will recognize that additional members of the foregoing list, obtainable by substitution of known ligands or different Group 3-10 metals for those specifically named, are also included within the invention. Moreover, it should also be recognized that all possible delocalized electronic distributions within the π-bonded, cyclic, ligand, such as $\eta^3$, $\eta^4$ or $\eta^5$ are intended to be included by the foregoing named compounds.

The complexes can be prepared by combining a Group 3-10, metal salt with the corresponding cyclic ligand silane amide dianion in an inert diluent, or by combining a metal amide with the corresponding neutral, cyclic, silane substituted ring system in an inert diluent. A reducing agent can be employed to produce the lower oxidation state complexes, and standard ligand exchange procedures can by used to produce different ligand substituents. Processes that are suitably adapted for use herein are well known to synthetic organometallic chemists. The syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum, zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; dialkylmagnesium compounds, and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri (hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis (fluoroaryl)borate, especially a tetrakis(pentafluorophenyl) borate. The foregoing activating cocatalysts and activating techniques have been previously taught with respect to different metal complexes in the following references: EP-A-277,003, U.S. Pat. Nos. 5,153,157, 5,064,802, 5,321, 106, 5,721,185, 5,350,723, 5,425,872, 5,625,087, 5,883,204, 5,919,983, 5,783,512, WO 99/15534, and U.S. Ser. No. 09/251,664, filed Feb. 17, 1999 (WO99/42467).

Combinations of neutral Lewis acids, especially the combination of a trialkylaluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Brønsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

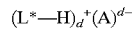

wherein:

L* is a neutral Lewis base;

(L*—H)$^+$ is a conjugate Brønsted acid of L*;

$A^{d-}$ is a noncoordinating, compatible anion having a charge of d−, and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula:

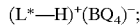

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium(hydroxyphenyl)tris(pentafluorophenyl)borate,
methylditetradecylammonium(diethylaluminoxyphenyl)tris(pentafluorophenyl)borate,
methyldihexadecylammonium tetrakis(pentafluorophenyl)borate,
methyldihexadecylammonium(hydroxyphenyl)tris(pentafluorophenyl)borate,
methyldihexadecylammonium(diethylaluminoxyphenyl)tris(pentafluorophenyl)borate,
methyldioctadecylammonium tetrakis(pentafluorophenyl)borate,
methyldioctadecylammonium(hydroxyphenyl)tris(pentafluorophenyl)borate,
methyldioctadecylammonium(diethylaluminoxyphenyl)tris(pentafluorophenyl)borate,
methyldioctadecylammonium tetrakis(pentafluorophenyl)borate,
phenyldioctadecylammonium tetrakis(pentafluorophenyl)borate,
phenyldioctadecylammonium(hydroxyphenyl)tris(pentafluorophenyl)borate,
phenyldioctadecylammonium(diethylaluminoxyphenyl)tris(pentafluorophenyl)borate,
(2,4,6-trimethylphenyl)dioctadecylammonium tetrakis(pentafluorophenyl)borate,
(2,4,6-trimethylphenyl)dioctadecylammonium(hydroxyphenyl)tris(pentafluorophenyl)borate,
(2,4,6-trimethylphenyl)dioctadecylammonium(diethylaluminoxyphenyl)tris(pentafluorophenyl)borate,
(2,4,6-trifluorophenyl)dioctadecylammonium tetrakis(pentafluorophenyl)borate,
(2,4,6-trifluorophenyl)dioctadecylammonium(hydroxyphenyl)tris(pentafluorophenyl)borate,
(2,4,6-trifluorophenyl)dioctadecylammonium(diethylaluminoxyphenyl)tris(pentafluorophenyl)borate,
(pentafluorophenyl)dioctadecylammonium tetrakis(pentafluorophenyl)borate,
(pentafluorophenyl)dioctadecylammonium(hydroxyphenyl)tris(pentafluorophenyl)borate,
(pentafluorophenyl)dioctadecylammonium(diethylaluminoxyphenyl)tris(pentafluorophenyl)borate,
(p-trifluoromethylphenyl)dioctadecylammonium tetrakis(pentafluorophenyl)borate,
(p-trifluoromethylphenyl)dioctadecylammonium(hydroxyphenyl)tris(pentafluorophenyl)borate,
(p-trifluoromethylphenyl)dioctadecylammonium(diethylaluminoxyphenyl)tris(penta-fluorophenyl)borate,
p-nitrophenyldioctadecylammonium tetrakis(pentafluorophenyl)borate,
p-nitrophenyldioctadecylammonium(hydroxyphenyl)tris(pentafluorophenyl)borate,
p-nitrophenyldioctadecylammonium(diethylaluminoxyphenyl)tris(pentafluorophenyl)borate,
and mixtures of the foregoing, dialkyl ammonium salts such as:
di-(i-propyl)ammonium tetrakis(pentafluorophenyl)borate, methyloctadecylammonium tetrakis(pentafluorophenyl)borate, methyloctadodecylammonium tetrakis(pentafluorophenyl)borate, and dioctadecylammonium tetrakis(pentafluorophenyl)borate;

tri-substituted phosphonium salts such as:
triphenylphosphonium tetrakis(pentafluorophenyl)borate, methyldioctadecylphosphonium tetrakis(pentafluorophenyl)borate, and tri(2,6-dimethylphenyl)phosphonium tetrakis(pentafluorophenyl)borate;

di-substituted oxonium salts such as:
diphenyloxonium tetrakis(pentafluorophenyl)borate, di(o-tolyl)oxonium tetrakis(pentafluorophenyl)borate, and di(octadecyl)oxonium tetrakis(pentafluorophenyl)borate;

di-substituted sulfonium salts such as:
di(o-tolyl)sulfonium tetrakis(pentafluorophenyl)borate, and methylcotadecylsulfonium tetrakis(pentafluorophenyl)borate.

Preferred trialkylammonium cations are methyldioctadecylammonium and dimethyloctadecylammonium. The use of the above Brønsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

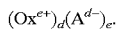

wherein:

$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$ or $Pb^{+2}$. Preferred embodiments of $A^{d-}$ are those anions previously defined with respect to the Brønsted acid containing activating cocatalysts, especially tetrakis (pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

wherein:

Ⓒ$^+$ is a $C_{1-20}$ carbenium ion; and
$A^-$ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

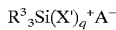

wherein:

$R^3$ is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula:

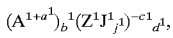

wherein:
$A^1$ is a cation of charge $+a^1$,
$Z^1$ is an anion group of from 1 to 50, preferably 1 to 30 atoms, not counting hydrogen atoms, further containing two or more Lewis base sites;
$J^1$ independently each occurrence is a Lewis acid coordinated to at least one Lewis base site of $Z^1$, and optionally two or more such $J^1$ groups may be joined together in a moiety having multiple Lewis acidic functionality,
$j^1$ is a number from 2 to 12 and
$a^1, b^1, c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

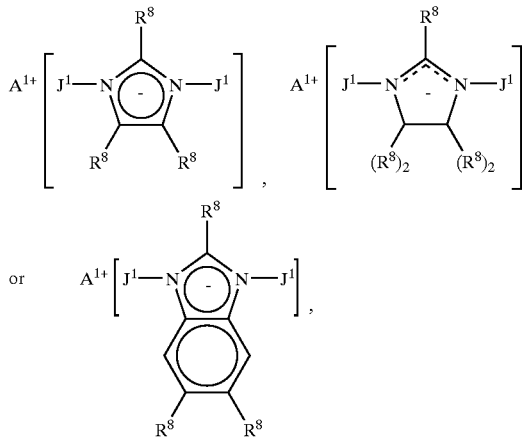

wherein:
$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl) ammonium-cation,
$R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and
$J^1$ is tris(pentafluorophenyl)borane or tris (pentafluorophenyl)aluminane.

Examples of these catalyst activators include the trihydrocarbylammonium-, especially, methylbis(tetradecyl) ammonium- or methylbis(octadecyl)ammonium-salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide, bis(tris(pentafluorophenyl) borane)-4,5-bis(undecyl)imidazolide,
bis(tris(pentafluorophenyl)borane)4,5-bis(heptadecyl) imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide, bis(tris(pentafluorophenyl) borane)-4,5-bis(undecyl)imidazolinide, bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide, bis(tris(pentafluorophenyl)alumane)4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide, bis(tris(pentafluorophenyl)alumane)-2-heptadecylimidazolinide, bis(tris(pentafluorophenyl)alumane)4,5-bis(undecyl)imidazolinide,
bis(tris(pentafluorophenyl)alumane)4,5-bis(heptadecyl)imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

A further class of suitable activating cocatalysts include cationic Group 13 salts corresponding to the formula:

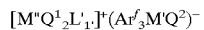

wherein:
M" is aluminum, gallium, or indium;
M' is boron or aluminum;
$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;
$Q^2$ is an alkyl group, optionally substituted with one or more cycloalkyl or aryl groups, said $Q^2$ having from 1 to 30 carbons;
L' is a monodentate or polydentate Lewis base, preferably L' is reversibly coordinated to the metal complex such that it may be displaced by an olefin monomer, more preferably L' is a monodentate Lewis base;
1' is a number greater than zero indicating the number of Lewis base moieties, L', and
$Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula: $[M"Q^1{}_2L'{}_{1'}]^+(Ar^f{}_3BQ^2)^-$, wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

As an alternative method of activation, the metal complexes may be exposed to electrochemical activation in the presence of a counter ion. Such a technique is previously known in the art, and disclosed, for example, in U.S. Pat. No. 5,372,682.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene; 1,4-hexadiene, and norbornadiene. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluorophenyl)borate, such as an ammonium salt of (4-hydroxy-3,5-ditertiarybutylphenyl)tris(pentafluorophenyl)borate or (4-hydroxyphenyl)-tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. The reactor temperature and pressure may be controlled by adjusting the solvent/monomer ratio, the catalyst addition rate, as well as by cooling or heating coils, jackets or any combination thereof. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mentioned chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than 0.5, preferably less than 0.2, more preferably less than 0.05, even more preferably less than 0.02 and may even be less than 0.01.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

All solvents were purified using the technique disclosed by Pangborn et al, *Organometallics*, 15, 1518–1520, (1996). $^1$H and $^{13}$C NMR shifts were referenced to internal solvent resonances and are reported relative to TMS.

Example 1

(tetramethylcyclopentadienyl)dimethyl(t-butylamido)silanetitanium (II) bis(tri(methylsilyl)) acetylene (IA)

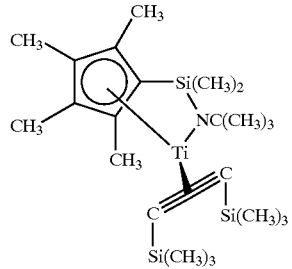

1.17 g (3.31 mmol) (tetramethylcyclopentadienyl) dimethyl(t-butylamido)titanium dichloride and 1.70 g (10.0 mmol)bis(TMS)acetylene were dissolved in 50 ml toluene, followed by addition of 1.93 g (3.64 mmol) butylethylmagnesium. After 1 hour of refluxing the solution was filtered through a pad of diatomaceous earth and the solvent was removed under vacuum. The resulting oil was redissolved in 10 ml hexane and filtered through a pad of diatomaceous earth. The pad was washed with 10 ml hexane twice before all the solvent volume was reduced under vacuum and the solution placed in the freezer over night. The next morning the product was collected as a violet precipitate.

$^1$H NMR ($C_6D_6$): [ppm] δ=−0.03 (s, 18H, TMSC= CTMS), 0.30 (s, 6H, Si(C$\underline{H}_3$)$_2$), 1.23, 2.65 (s, 12H, Cp (C$\underline{H}_3$)$_4$), 2.14 (s, 9H, t-Bu).

$^{13}$C NMR ($C_6D_6$): [ppm] δ=1.28, 6.83, 13.07, 13.79, 38.08, 57.79, 130.27, 133.64.

Polymerization General Conditions

Mixed alkanes and liquid olefins are purified by sparging with purified nitrogen followed by passage through columns containing alumina (A-2, available from LaRoche Inc.) and Q5 reactant (available from Englehard Chemicals Inc.) at 50 psig using a purified nitrogen pad. All transfers of solvents and solutions described below are accomplished using a gaseous pad of dry, purified nitrogen or argon. Gaseous feeds to the reactor are purified by passage through columns of A-204 alumina (available from LaRoche Inc.) and Q5 reactant. The aluminas are previously activated by treatment at 375° C. with nitrogen, and Q5 reactant is activated by treatment at 200° C. with 5 percent hydrogen in nitrogen.

Ethylene Polymerization

A stirred, two-liter Parr reactor was charged with approximately 433 g of mixed hexanes. Hydrogen was added as a molecular weight control agent by differential pressure expansion from a 75 mL addition tank at 50 psig (345 kPa). The reactor was heated to 90° C. and saturated with ethylene at 200 psig (1.4 MPa). The appropriate amount of catalyst and cocatalyst as 0.005M solutions in toluene were premixed in a glovebox and transferred to a catalyst addition tank and injected into the reactor. After 10 minutes reaction with ethylene on demand the increase in reactor temperature was recorded and the reaction terminated.

The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation). Polymers formed are dried in a programmed vacuum oven with a maximum temperature of 140° C. and a 20 hour heating period. The metal complex of the invention demonstrated from 10 to 50 percent improvement based on catalyst efficiency over the comparative examples. The results are contained in Table 1.

TABLE 1

| Run | Cat. (μmol) | Cocatalyst (μmol) | Exotherm (° C.) | Maximum $C_2H_4$ flow (g/min) | eff.[1] |
|---|---|---|---|---|---|
| 1* | TTTi[2] (2.5) | FAB[3] (7.5)/ MAO[4] (25.0) | 4.9 | 7.9 | 0.66 |
| 2 | Ex. 1 (2.5) | FAB[3] (7.5)/ MAO[4] (25.0) | 5.6 | 38.5 | 0.74 |
| 3* | TTTi[2] (2.0) | BAU[5] (7.5)/ MAO (20.0) | 8.3 | 26.3 | 0.66 |

TABLE 1-continued

| Run | Cat. (μmol) | Cocatalyst (μmol) | Exotherm (° C.) | Maximum C$_2$H$_4$ flow (g/min) | eff.[1] |
|---|---|---|---|---|---|
| 4 | Ex. 1 (2.0) | BAU[5] (7.5)/ MAO (20.0) | 28.9 | 59.5 | 1.00 |

*Comparative, not an example of the invention
[1]efficiency, g polymer/μg Ti
[2](tetramethylcyclopentadienyl)dimethyl(t-butylamido)silanetitanium (II) 1,4-diphenyl-1,3-butadiene
[3]tris(pentafluorophenyl)borane
[4]modified methylalumoxane available from Akzo Chemicals
[5]bis(tris(pentafluorophenyl)alumane)-2-undecylimidazolide, prepared according to the teachings of WO99/03413

What is claimed is:

1. A metal complex corresponding to the formula:

CpM(ZY)L    (I), where Cp is a neutral or anionic ligand group containing at least on cyclic group containing delocalized π-electrons, by means of which Cp is bonded to M;

M is a Group 4 metal of the Periodic Table of the Elements;

ZY is a linking group with Z bonded to Cp and Y bonded to M, and wherein Z is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L"$, $SnR^6_2$, or $GeR^6_2$, and Y is —O—, —S—, —NR$^5$—, —PR$^5$—; —NR$^5_2$, or —PR$^5_2$;

R$^5$, independently each occurrence, is hydrocarbyl, trihydrocarbylsilyl, or trihydrocarbylsilylhydrocarbyl, said R$^5$ having up to 20 atoms not counting hydrogen, and optionally two R$^5$ groups together with the remainder of Y form a ring system;

R$^6$, independently each occurrence, is hydrogen, or a member selected from hydrocarbyl, hydrocarbyloxy, silyl, halogenated alkyl, halogenated aryl, —NR$^7_2$, and combinations thereof, said R$^6$ having up to 20 atoms not counting hydrogen, and optionally, one or more R$^6$ groups together with the remainder of Z form a ring system;

R$^7$ independently each occurrence is hydrocarbyl or two R$^7$ groups together with N form a ring system, said R$^7$ having up to 10 atoms not counting hydrogen;

L" is a monodentate or polydentate Lewis base optionally bonded to R$^6$; and

L is acetylene, or a mono- or di-substituted derivative of acetylene.

2. The metal complex of claim 1 wherein Cp is a cyclopentadienyl group or a hydrocarbyl substituted derivative thereof.

3. The metal complex of claim 1 corresponding to the formula;

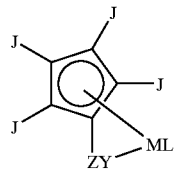

(IA)

wherein

M is a group 4 metal;

Y is NR$^5$, wherein R$^5$ is C$_{1-10}$ alkyl or cycloalkyl;

Z is dimethylsilane;

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and optionally two J groups together may form a divalent derivative thereby forming a saturated or unsaturated ring; and L is a disubstituted acetylene compound of the formula, J'C≡CJ', wherein J' is hydrocarbyl or tri(hydrocarbylsilyl) of up to 10 atoms not counting hydrogen.

4. The metal complex of claim 1 selected from the group consisting of:

(tetramethylcyclopentadienyl)-N-(1,1-dimethylethyl) dimethylsilanamide titanium (II) 1,2-bis(trimethylsilyl) acetylene, (tetramethylcyclopentadienyl)-N-(cyclohexyl) dimethylsilanamide titanium (II) 1,2-bis(trimethylsily) acetylene, (inden-1-yl)-N-(1,1-dimethylethyl)dimethylsilanamide titanium (II) 1,2-bis(trimethylsilyl)acetylene, (inden-1-yl)-N-(cyclohexyl)dimethylsilanamide titanium (II) 1,2-bis(trimethylsilyl)acetylene, (2-methyl-4-phenylinden-1-yl)-N-(1,1-dimethylethyl) dimethylsilanamide titanium (II) 1,2-bis(trimethylsilyl) acetylene, (2-methyl-4-phenylinden-1-yl)-N-(cyclohexyl) dimethylsilanamide titanium (II) 1,2-bis(trimethylsilyl) acetylene, (2-methyl-4-naphthylinden-1-yl)-N-(1,1-dimethylethyl) dimethylsilanamide titanium (II) 1,2-bis(trimethylsilyl) acetylene, (2-methyl-4-naphthylinden-1-yl)-N-(cyclohexyl) dimethylsilanamide titanium (II) 1,2-bis(trimethylsilyl) acetylene, (3-(N,N-dimethylamino)inden-1-yl)-N-(1,1-dimethylsilanamide titanium (II) 1,2-bis(trimethylsilyl) acetylene, (3-(N,N-dimethylamino)inden-1-yl)-N-(cyclohexyl) dimethylsilanamide titanium (II) 1,2-bis(trimethylsilyl) acetylene, (3-(N,N-dimethylamino)inden-1-yl)-N-(1,1-dimethylethyl)dimethylsilanamide titanium (II) 1,2-bis(trimethylsilyl)acetylene, (3-(N-pyrrolidino)inden-1-yl)-N-(cyclohexyl) dimethylsilanamide titanium (II) 1,2-bis(trimethylsilyl)acetylene, (3-(N-pyrrolidino)inden-1-yl)-N-(1,1-dimethylethyl) dimethylsilanamide titanium (II) 1,2-bis(trimethylsilyl)acetylene, (3-(N,N-dimethylamino)inden-1-yl)-N-(cyclohexyl) dimethylsilanamide titanium (II) 1,2-bis(trimethylsilyl)acetylene, (s-indacen-1-yl)-N-(1,1-dimethylethyl) dimethylsilanamide titanium (II) 1,2-bis(trimethylsilyl)acetylene, (s-indacen-1-yl)-N-(cyclohexyl)dimethylsilanamide titanium (II) 1,2-bis(trimethylsilyl)acetylene, (3,4-(cyclopenta(l)phenantrathen-2-yl)-N-(1,1-dimethylethyl)dimethylsilanamide titanium (II) 1,2-bis(trimethylsilyl)acetylene, (3,4-(cyclopenta(l)phenantrathen-2-yl)-N-(cyclohexyl) dimethylsilanamide titanium (II) 1,2-bis(trimethylsilyl)acetylene, (2,8-dihydrodibenzo[e,h]azulen-2-yl)-N-(1,1-dimethylethyl)dimethylsilanamide titanium (II) 1,2-bis(trimethylsilyl)acetylene, (2,8-dihydrodibenzo[e,h]azulen-2-yl)-N-(cyclohexyl) dimethylsilanamide titanium (II) 1,2-bis(trimethylsilyl)acetylene, and mixtures thereof.

5. A catalyst for addition polymerizations comprising:
A. i) a metal complex according to any one of claims 1–4, and
   ii) an activating cocatalyst,
the molar ratio of i) to ii) being from 1:10,000 to 100:1, or
B. the reaction product formed by converting a metal complex of any one of claims 1–4 to an active catalyst by use of the foregoing combination or by use of an activating technique.

6. The catalyst of claim 5 additionally comprising a support.

7. A process for the polymerization of addition polymerizable monomers comprising contacting the monomer or mixture of monomers under polymerization conditions with a catalyst according to claim 5.

8. A process for the polymerization of addition polymerizable monomers comprising contacting the monomer or mixture of monomers under polymerization conditions with a catalyst according to claim 6.

9. The process of claim 7 which is a solution polymerization process.

10. The process of claim 8 which is a slurry polymerization.

11. The process of claim 8 which is a gas phase polymerization.

* * * * *